United States Patent
Gee (10) Patent No.: US 9,176,125 B2
(45) Date of Patent: Nov. 3, 2015

(54) PRODUCTION OF CONJUGATES

(75) Inventor: Nicholas Gee, Cambridge (GB)

(73) Assignee: Innova Biosciences Limited, Cambridge (GB)

( * ) Notice: Subject to any disclaimer, the term of this patent is extended or adjusted under 35 U.S.C. 154(b) by 0 days.

(21) Appl. No.: 12/664,147

(22) PCT Filed: Jun. 12, 2008

(86) PCT No.: PCT/GB2008/050438
§ 371 (c)(1),
(2), (4) Date: Dec. 23, 2009

(87) PCT Pub. No.: WO2008/152424
PCT Pub. Date: Dec. 18, 2008

(65) Prior Publication Data
US 2010/0184184 A1    Jul. 22, 2010

(30) Foreign Application Priority Data
Jun. 14, 2007    (GB) .................................. 0711560.3

(51) Int. Cl.
*G01N 33/532*    (2006.01)

(52) U.S. Cl.
CPC ..................... *G01N 33/532* (2013.01)

(58) Field of Classification Search
None
See application file for complete search history.

(56) References Cited

U.S. PATENT DOCUMENTS

| 2002/0168667 A1* | 11/2002 | Kinoshita et al. | 435/6 |
| 2005/0106649 A1 | 5/2005 | Tsao et al. | 435/8 |

FOREIGN PATENT DOCUMENTS

| WO | WO 02/083937 | 10/2002 | ............... C12Q 1/48 |
| WO | WO 03/035830 | 5/2003 | |

OTHER PUBLICATIONS

Bonifaz et al. (Efficient Targeting of Protein Antigen to the Dendritic Cell Receptor DEC-205 in the Steady State Leads to Antigen Presentation on Major Histocompatibility Complex Class I Products and Peripheral CD8+T Cell Tolerance., J. Exp. Med, 2002, vol. 196(12), pp. 1627-1638.*
Sulfo-SMCC from Thermo Scientific Pierce Protein Research Products (last viewed on Aug. 30, 2011).*
Polyketide (last viewed on Dec. 22, 2011).*
Urisu et al., Allergenic activity of heated and ovomucoid-depleted egg white, Journal of Allergy and Clinical Immunology., vol. 100, Issue 2, (Aug. 1997), pp. 171-176.*
Neova technologies (last viewed on Dec. 22, 2011).*
2-Iminothiolane from Sigma (May 2003).*
Kamps-Holtzapple et al., Development of a Monoclonal Antibody-Based ELISA for the Anthelmintic Hygromycin B., J. Agric. Food Chem., (1994), vol. 42, pp. 822-827.*

(Continued)

*Primary Examiner* — Alexander Kim
(74) *Attorney, Agent, or Firm* — Morgan, Lewis & Bockius LLP (57) ABSTRACT

Disclosed is a method for indirectly coupling a small molecule ligand to a molecule to be labelled with the ligand, the method comprising the step of: contacting a scaffold molecule, to which is attached at least one small molecule ligand, with the molecule to be labelled, the scaffold molecule having at least one group which is reactive towards a receiver moiety present or formed in situ on the molecule to be labelled, so as to form a bond between the scaffold molecule and the molecule to be labelled, thereby indirectly coupling the small molecule ligand to the molecule to be labelled.

11 Claims, 7 Drawing Sheets

(56) References Cited

OTHER PUBLICATIONS

Rose et al., Competitive Indirect ELISA for Ceftiofur Sodium and the Effect of Different Immunizing and Coating Antigen Conjugates., Bioconjugate Chem., 1995, vol. 6 (5), pp. 529-535.*

Perlmutter et al., Subclass Restriction of Murine Anti-Carbohydrate Antibodies1., The Journal of Immunology, (1978), vol. 121, pp. 566-572.*

Albinsson et al. (Near-ultraviolet electronic transitions of the tryptophan chromophore: linear dichroism, fluorescence anisotropy, and magnetic circular dichroism spectra of some indole derivatives, J. Phys. Chem., (1989), vol. 93 (18), pp. 6646-6654.*

Langer et al. (Preparation of avidin-labeled protein nanoparticles as carriers for biotinylated peptide nucleic acid, European Journal of Pharmaceutics and Biopharmaceutics (2000), vol. 49, Issue 3, pp. 303-307.*

Oi et al., Fluorescent phycobiliprotein conjugates for analyses of cells and molecules., JCB (1982), vol. 93, No. 3, pp. 981-986.*

Chung et al., Incomplete Activation of CD4 T Cells by Antigen-Presenting Transitional Immature B Cells: Implications for Peripheral B and T Cell Responsiveness., The Journal of Immunology (2003), vol. 171 No. 4, pp. 1758-1767.*

Pikal, Freeze-Drying of Proteins Process, Formulation, and Stability; ACS Symposium Series, vol. 567; Lilly Research Laboratories, Eli Lilly and Company, Indianapolis, IN 46285; Formulation and Delivery of Proteins and Peptides; 1994 American Chemical Society; Chapter 8, pp. 120-133.*

McCall et al., "Simplified Method for Conjugating Macrocyclic Bifunctional Chelating Agents to Antibodies via 2 Iminothiolane", Bioconjugate Chemistry, ACS, Washington, D.C., 1(3):222-226 (Jan. 1, 1990).

Pechar et al., "Poly(ethylene glycol)-doxorubicin conjugates with pH-controlled activation", Journal of Bioactive and Compatible Polymers, 20(4):319-341 (Jul. 4, 2005).

Chan, et al., "Proteomic analysis of redox- and ErbB2-dependent changes in mammary luminal epithelial cells using cysteine- and lysine-labelling two-dimensional difference gel electrophoresis", Proteomics, 5(11)2908-2926 (Jul. 2005).

Vaidyanathan et al., "N-epsilon-(3-[*l]iodobenzoyl)-Lys(5)-N-alpha-maleimido-Gly(1)-GEEEK ([l]IB-Mal-0-GEEEK): A radioiodinated prosthetic group containing negatively charged D-glutamates for labeling internalizing monoclonal antibodies", Bioconjugate Chemistry, 17(4):1085-1092 (Jul. 4, 2006).

Garnett et al. "Preparation and properties of a drug-carrier-antibody conjugate showing selective antibody-directed cytotoxicity in vitro." Int. J. Cancer 31: 661-670, 1983.

Kerr et al., "Antibody-penicillin-V-amidase conjugates kill antigen-positive tumor cells when combined with doxorubicin phenoxyacetamide," Cancer Immunol Immunother, 31: 202-206 (1990).

* cited by examiner

PRODUCTION OF CONJUGATES

This application is a 371 filing of PCT/GB2008/050438 (WO 2008/152424), filed Jun. 12, 2008, claiming priority benefit of GB 0711560.3, filed Jun. 14, 2007.

FIELD OF THE INVENTION

This invention relates to a method of indirectly labelling a molecule, reagents and kits of use in the method, and a conjugate produced by the method.

BACKGROUND OF THE INVENTION

The need to conjugate biomolecules with labels is found in all areas of bioscience research, diagnostics and medicine. Labels that are attached to biomolecules include proteins (e.g. enzymes, fluorescent proteins, streptavidin), oligonucleotides and small-molecule ligands (SMLs; singular SML) usually with molecular weights of less than 1000 (e.g. biotin, fluorescent dyes, metal ion chelators, photoreactive groups, iodinatable molecules, photosensitisers, quenchers, short peptides and drugs). SMLs that are employed in conjugation reactions usually, but not always, have a reactive (often amine-reactive [AR]) group that facilitates attachment of the SML to the biomolecule. For example, fluorescein is normally introduced using an isothiocyanate derivative (FITC; fluorescein isothiocyanate) or an N-hydroxysuccinimide (NHS) derivative.

The majority of activated SMLs used in conjugation reactions are NHS esters, which have a number of attractive features, such as facile coupling to amines at physiological pH. This generates an amide link that is both strong and irreversible. Disadvantageously, NHS esters are prone to decomposition on storage, especially if moisture enters the product, and they are very susceptible to hydrolysis in aqueous solutions. As SMLs are monovalent with respect to the reactive moiety, the loss of any reactive groups reduces the percentage of SML that can participate in conjugation reactions. Because of possible decomposition on storage and because of competing hydrolysis reactions, the SML is generally used in a significant molar excess. As many biomolecules contain multiple amine functions, trial experiments are usually carried out on a small scale with varying molar ratios and/or varying reaction times to optimise the conditions and to avoid over-labelling. Finally, with the need to use a significant excess of SML, it is inevitable that large amounts of unconjugated SML and/or hydrolysis products will contaminate the final product, and that purification of the conjugate will be required.

An alternative chemistry that avoids some of the problems encountered with NHS esters involves thiol-mediated coupling of molecules. Thiol-reactive (TR) SMLs are relatively stable but because of their more limited commercial availability and because many biomolecules lack of indigenous free thiols TR-SMLs are less frequently used in conjugation reactions. While methods to introduce thiols into biomolecules are known, the operation of adding thiol groups usually makes the process of conjugation technically more complicated. Functional groups found in commercially available SMLs that react with thiol groups include maleimide, iodoacetyl, bromoacetyl, aziridine, epoxide, acryloyl, and thiol-disulfide exchange reagents (e.g. pyridyl disulfides).

The present invention relates to, inter alia, methods for making conjugates that circumvent at least some of the problems associated with reactive SMLs, particularly NHS esters, and with other SMLs that are monovalent with respect to their reactive functional groups. These methods are described more fully below.

SUMMARY OF THE INVENTION

Typically, in the present invention, one, two or more reactive SMLs, each in limiting amounts, are contacted under suitable conditions with a solution of a large scaffold molecule that has multiple nucleophilic groups. These groups may be of the same type or of many types. In molar terms, the nucleophilic groups are in considerable excess over SMLs and only a proportion of the nucleophilic groups react. The remaining groups are then contacted with another molecule (an "activator") that reacts at multiple sites to attach significant numbers of thiol-reactive (TR) functions to the scaffold. The resulting activated SML-scaffold conjugate contains 0–n SMLs on average (where n is a number>0) and is polyvalent with respect to TR functions. The poly-TR scaffold is purified by desalting or dialysis and then linked in the presence of 2-iminothiolane at close to physiological pH to a molecule or biomolecule (e.g. antibody) that has amine functionality. 2-iminothiolane creates in situ the thiol functions on the biomolecule necessary to effect conjugation to the scaffold (see WO 2007/068906).

In a first aspect, the invention provides a method for indirectly coupling a small molecule ligand to a molecule to be labelled with the ligand, the method comprising the steps of: contacting a scaffold molecule, to which is attached at least one small molecule ligand, with the molecule to be labelled, the scaffold molecule having at least one group which is reactive towards a receiver moiety present or formed in situ on the molecule to be labelled, so as to form a bond between the scaffold molecule and the molecule to be labelled, thereby indirectly coupling the small molecule ligand to the molecule to be labelled. The linked combination of small molecule ligand(s), scaffold and molecule to be labelled may be referred to generally as a "conjugate".

Preferably the scaffold molecule will compromise a plurality of groups reactive towards the receiver moiety present or formed on the molecule to be labelled. In a preferred embodiment the scaffold molecule comprises one or more (preferably a plurality) of thiol-reactive ("TR") groups which are reactive towards thiol receiver moieties present or formed in situ on the molecule to be labelled.

In a preferred embodiement, thiol receiver moieties are formed as the molecule to be labelled by the action of a thiol generator ("TG") which contains at least one sulphur atom and which reacts with the molecule to be labelled to produce a covalently bound sulfhydryl or thiol group thereon, the sulfhydryl group including a sulphur atom donated by the thiol generator. The thiolation reaction typically involves thiolation of a nucleophilic group, such as an amine (especially a primary amine) or a hydroxyl group. Thiolation of the molecule to be labelled is most conveniently performed in situ, using techniques described in WO 2007/068906. A preferred TG is 2-iminothiolane (2-IT)(also known as Traut's reagent), which can react with e.g. the amine groups present in polypeptides (which the molecule to be indirectly labelled will normally comprise). 2-IT is fully water-soluble and reacts with primary amines in the pH range 7 to 10. In conventional conjugate formation reactions, 2-IT is used at a pH of about 8, under which conditions 2-IT reacts efficiently and rapidly with primary amines, e.g. in lysine residues present in peptides, polypeptides and proteins. For reaction with primary amines, it has now been found that it is preferable to react 2-IT at a pH lower than the conventional valve of 8. Thus when using 2-IT the conjugation reaction is preferably carried out at a pH less than 8, preferably less than 7.8 and more preferably less than pH 7.7. A preferred pH range is 7.0-7.5. Since the reactions of thiols with many types of thiol-reactive groups take place efficiently between pH 6.5 and 7.5, it is undesirable to use 2-IT at high pH values where competing hydrolysis reactions generate undesirable free thiols. Moreover, the thiol-reactive groups may also be subject to hydrolysis reactions at alkaline pH, or may show reduced selectivity for thiols, as in the case of the popular maleimide functional group.

Suitable buffering components for use in the thiolation step phosphate buffers, especially sodium phosphate, N-(2-Hydroxyethyl)piperazine-N'-(2-ethanesulfonic acid) (HEPES), 2-morpholinoethanesulfonic acid (MES), 3-(N-morpholino) propanesulfonic acid (MOPS), bicarbonate and other buffers that do not react with the thiol generator, or react relatively slowly when compared with the rate of reaction of TG with functional groups on the molecule to be labelled. The list may therefore contain amine-containing buffers that react at a suitably slow rate.

Other components of the final conjugation reaction mix may include salts (e.g NaCl) and other inorganic or organic components that do not directly participate in the reactions but provide a suitable environment that stabilises components or in some other way facilitate the desired reactions or minimise losses, for example, on the surfaces of vessels.

Since the TG is reactive it may react with other nucleophiles in the conjugation mixture. Water is a weak nucleophile but it is typically present at a high concentration and hydrolysis reactions could increase the concentration of thiols not covalently associated with the molecule to be labelled, especially at pH values significantly above pH 7.

Preferably the TG includes little or no free thiol groups, with the level suitably being below 5% in molar terms, preferably below 3% in molar terms and more preferably below 1% in molar terms.

2-IT from commercial sources may contain significant quantities of free thiol, and free thiols may also be generated over a period of time in storage. Free thiols could compete with those formed on the molecule to be labelled for the thiol-reactive groups on the scaffold and so reduce conjugation efficiency. In the case of 2-iminothiolane, one supplier states that contamination with free thiols is 'up to 5%'. The batches used for work described herein were measured at about 1% thiol content in molar terms.

It is preferred that the molar ratios of the reactants are carefully selected so that small quantities of free thiols possibly present in the TG do not impact significantly on conjugation efficiency. 2-IT is more stable than most other molecules that are used to introduce thiols or protected thiols and it is not necessary to use large molar excess. Some amine-reactive heterobifunctional reagents with NHS groups have short half-lives in aqueous solutions and are used in large excess to compensate for rapid hydrolysis. Typically, the TG is used in reasonable excess, e.g. 10 times molar excess over the relevant chemical functionality, such as amines, present on the molecule to be labelled to ensure that all molecules thereof are thiolated. However, in selecting a suitable concentration of TG the user must have regard for the likely rate of reaction, which is influenced by the pH of the solution. A suitable concentration of TG at a fixed pH is readily determined by examining the effect of varying the concentration of TG on the performance of the resulting conjugates. It is preferred that the reaction conditions allow efficient thiolation of the molecule to be indirectly labelled, but that excessive thiolation is avoided so as not to damage any biological activity of the molecule. Equally, excessive amounts of the scaffold molecule should not be attached to the molecule to be indirectly labelled, otherwise this might lead to suboptimal performance of the conjugate. The scaffold molecule is typically present in modest excess, e.g. up to about 5 times molar excess, in relation to the molecule to be indirectly labelled, but optimal molar ratios may depend on the application to which the conjugate is to be put. The optimal ratio of reactants may readily be determined for any particular conjugate by performing initial trial reactions with, say, low, medium and high ratios, and then "fine-tuning" the ratios by trial and error.

The scaffold molecule will preferably comprise a plurality of reactive groups which are reactive towards the receiver moiety present or formed on the molecule to be labelled. Such groups may be present ab initio or may be introduced into the scaffold molecule as part of the method of the invention. Conveniently the scaffold molecule comprises a plurality of reactive groups which are reactive towards a functional group present on the small molecule ligand. The reactive groups reactive towards the small molecule ligand may be of the same type as, or different from, the reactive groups which are reactive towards to the receiver moiety present or formed on the molecule to be labelled.

In a preferred embodiment the scaffold molecule comprises a plurality of nucleophilic groups. In a preferred embodiment the scaffold comprises a plurality of amine groups, which may be reacted with an "activator" agent, as explained in greater detail below, to introduce thiol-reactive groups. In a preferred embodiment the scaffold molecule, prior to any coupling thereto of the small molecule ligand(s), has a molecular weight of at least 5 kD, more preferably at least 10 kD, and most preferably at least 20 kD.

In a preferred embodiment, the scaffold comprises a polymer, either naturally occurring or man made. In a preferred embodiment the polymer has multiple nucleophilic groups (or can be modified so that it contains the required number and type of nucleophilic groups). Scaffolds may have a single type of nucleophilic group or may have multiplicity of nucleophilic groups, as is typically found in some naturally occurring biomolecules, such as proteins.

Preferred polymers include polypeptides, dextrans aminated or derivatised (e.g. aminated) dextrans, thiolated polymers, activated polyethylene glycols, dendrimers, activated beads, nanoparticles or other particles. Particularly preferred polymers are polypeptides (i.e. polymers of amino acids), which are attractive because of their numerous and varied functional groups (amines, carboxyls, phenolates), providing a multiplicity of options for attaching SMLs and other molecules. In some embodiments Ovalbumin is preferred because of its (i) very high solubility in DMSO, which allows reactions with NHS esters of hydrophobic SMLs to be carried out in aqueous/organic mixtures without precipitation of either the SML or ovalbumin; and (ii) it has an optimal or near-optimal number of free online groups available for reaction. Another particularly preferred scaffold is dextran or a dextran derivative (e.g. aminated dextran) because of the ease with which suitable functional groups can be introduced and the broad range of sizes available. For present purposes, a "dextran derivative" is a molecule of dextran in which some, but usually not all, of the side chains of the polymer have been substituted by alternative moieties e.g. amine groups, alkoxy groups or the like.

The small molecule ligand may conveniently be selected from the group consisting of: fluorophores; chromophores; biotin; avidin; metal ion chelators; photoreactive groups; iodinatable moieties; photosensitisers; quenchers; peptides; and low molecular weight drugs. In particular, reactive forms of SMLs that may be used include NHS esters, isothiocyanates, triazines, sulfonyl chlorides, acyl azides, aryl halides, aldehydes, tetrafluorophenyl esters, imidoesters, maleimides, haloacetyl derivatives and hydrazides. The above list is not meant to be limiting and any SML with other functional groups (e.g. primary amines) that can be coupled to a suitable scaffold may be employed. Preferably the SML comprised a fluorescent dye. A selection of suitable fluorescent dyes and other molecules is given below, though again this is not intended to be limiting: 5-(and-6)-Carboxyfluorescein; 5-(and-6)-Carboxyrhodamine 110; 5-(and-6)-Carboxyrhodamine 6G; 5-(and-6)-Carboxytetramethylrhodamine; 5-(and-6)-Carboxy-X-rhodamine; 5-Carboxyfluorescein (5-FAM); 5-Carboxyrhodamine 110; 5-Carboxyrhodamine 6G; 5-Carboxytetramethylrhodamine; 5-Carboxy-X-rhodamine; 6-((7-Amino-4-methylcoumarin-3-acetyl) amino)hexanoic acid; 6-(Fluorescein-5-carboxamido) hexanoic acid; 6-carboxy-2",4,4",5",7,7"-hexachlorofluorescein; 6-Carboxy-4",5"-dichloro-2",7"-dimethoxyfluorescein (JOE); 6-Carboxyfluorescein (6-FAM); 6-Carboxyrhodamine 110; 6-Carboxyrhodamine 6G; 6-Carboxytetramethylrhodamine; 6-Carboxy-X-rhodamine; 7-Hydroxycoumarin-3-carboxylic acid; 7-Methoxycoumarin; Alexa Fluor 350; Alexa Fluor 405; Alexa Fluor 430; Alexa Fluor 488; Alexa Fluor 514; Alexa Fluor 532; Alexa Fluor 546; Alexa Fluor 555; Alexa Fluor 568; Alexa Fluor 594; Alexa Fluor 633; Alexa Fluor 647; Alexa Fluor 660; Alexa Fluor 680; Alexa Fluor 700; Alexa Fluor 750; Alexa Fluor 790; AMCA (7-amino-4-methylcoumarin-3-acetic acid); ATTO 390; ATTO 425; ATTO 465; ATTO 488; ATTO 495; ATTO 520; ATTO 532; ATTO 550; ATTO 565; ATTO 590; ATTO 594; ATTO 610; ATTO 611X; ATTO 620; ATTO 633; ATTO 635; ATTO 637; ATTO 647; ATTO 647N; ATTO 655; ATTO 680; ATTO 700; ATTO 725; ATTO 740; Bodipy dyes; Cascade Blue; Cascade Yellow; Chromeo 488; Chromeo 494; Chromeo 546; Chromeo 642; Cy2 bis; Cy3 mono; Cy3.5 mono; Cy5 mono; Cy5.5 mono; Cy7 mono; DyLight 488; DyLight 549; DyLight 549; DyLight 649; DyLight 680; DyLight 800; Fluorescein; HiLyte Fluor 488; HiLyte Fluor 555; HiLyte Fluor 647; HiLyte Fluor 680; HiLyte Fluor 750; IRDye 700DX; IRDye 800CW; IRDye 800RS; Lucifer yellow; Marina Blue; Oregon Green 488; Pacific Blue; Pacific Orange; PF-415; PF-488; PF-488-LSS; PF-500-LSS; PF-505; PF-510-LSS; PF-514-LSS; PF-520-LSS; PF-546; PF-555; PF-590; PF-610; PF-633; PF-647; PF-680; PF-700; PF-750; PF-780; PURETIME 14; PURETIME 20; PURETIME 22; PURETIME 325; Pyrene (and related analogues); Rhodamine B; Sulforhodamine 101; Sulforhodamine B (Lissamine rhodamine); Tetramethylrhodamine. Other useful SMLs include biotin, long chains analogues of biotin, iminobiotin, and chelators such as $N_1$-(p-isothiocyanotobenzyl)-diethylenetriamine-$N_1,N_2,N_3,N_3$-tetraacetic acid (DTTA).

While the attachment of SML to a scaffold substantially increases the effective molecular weight of the SML (typically by a factor of 100 or more) it is not uncommon for conjugation reactions to be carried out with large biomolecules. For example, one of the most frequently used labels in the immunodiagnostics field is horseradish peroxidase (HRP), which is of a similar size to the ovalbumin scaffold (40,000 versus 46,000). Other commonly used high molecular weight labels include allo-phycocyanin (Mr 105,000), alkaline phosphatase (Mr=160,000) and phycoerythrin (Mr=240,000). Thiol chemistry has proved particularly useful for these reactions; the label is first modified with a TR group (usually maleimide) and the other biomolecule is modified to introduce free thiols.

The terms "thiol-reactive" and "amine-reactive" as used herein are intended to designate moieties or, more especially, chemical groups which will react, under suitable conditions, with thiol groups (—SH) or amine groups (especially primary amine groups —$NH_2$) respectively. It should be noted that a "thiol-reactive" group will not necessarily react exclusively with thiol groups, and "amine-reactive" groups will not necessarily react exclusively with amine groups. In particular, a chemical group may possibly be both "thiol-reactive" and "amine-reactive", although it may exhibit one tendency more than the other e.g. depending on pH or other environmental factor prevailing at the time.

In a preferred embodiment, a heterobifunctional activator reagent is used to introduce thiol-reactive groups into the scaffold molecule. Conveniently the scaffold molecule comprises a plurality of amine groups which can react with the activator reagent. Examples of amine- and thiol-reactive heterobifunctional reagents include: N-succinimidyl 3-(2 pyridyldithio) propionate (SPDP); variants of SPDP with extended spacers (LC-SPDP; LC='long chain') and sulfo groups to increase aqueous solubility (sulfo-LC-SPDP); succinimidyloxycarbonyl-α-methyl-α-(2-pyridyldithio)toluene (SMPT); sulfo-LC-SMPT; succinimidyl-4-(N-maleimidomethyl)cyclohexane-1-carboxylate (SMCC); sulfo-SMCC; m-Maleimidobenzoyl-N-hydroxysuccinimide ester (MBS); sulfo-MBS; N-succinimidyl(4-iodoacetyl)aminobenzoate (SLAB); sulfo-SLAB; succinimidyl-4-(p-maleimidophenyl) butyrate (SMBP); sulfo-SMBP; N-(γ-Maleimidobutyryloxy) succinimide ester (GMBS); sulfo-GMBS; succinimidyl-6-((iodoacetyl)amino)hexanoate (SIAX); and its extended spacer form SIAXX; succinimidyl 4-(((iodoacetyl)amino) methyl)cyclohexane-1-carboxylate (SIAC); and its extended spacer form (SIACX); p-Nitrophenyl iodoacetate (NPIA). There are many other related examples, such as the carbonyl and sulfhydryl-reactive linker, β-maleimidopropionic acid hydrazide (BMPH).

The molecule to be indirectly labelled may be any molecule of interest, but will typically be fairly large (molecular weight of at least 25 kD, more typically at least 35 kD, and most typically at least 45 kD). In particular the molecule to be indirectly labelled will frequently comprise a polypeptide, such as an enzyme, or structural protein, receptor or cell-surface marker, or an antibody or antigen-binding fragment or variant thereof (such as an $F_v$, $F_{ab}$, scFv, a single domain antibody, bispecific or chimeric antibody or the like).

One, two or more steps (typically all) of the method of the invention are performed with one or more (typically all) of the reagents in solution. The solution may be entirely aqueous (that is, one in which water is essentially the only solvent) or may be partially aqueous (that is, a solution in which one or more other solvents may be present), or wholly organic (that is, a solution in which essentially the only solvent/s is/are not water). Preferably the solutions will be entirely or partially aqueous. Particularly convenient are solutions which comprise water and DMSO in any desirable ratio. In particular, each of the ligand, the molecule to be indirectly labelled, and the scaffold molecule will preferably be free in solution, not present as a solid phase or otherwise immobilised to a support or the like. This confers optimal reaction kinetics.

In a second aspect the invention provides a scaffold molecule for use in the method of the first aspect, the scaffold comprising one or more attached small molecule ligands and one or more groups reactive towards a receiver moiety present or formed in situ on the molecule to be labelled.

The small molecule ligand may be attached to the scaffold covalently (which is generally preferred) or non-covalently. If desired, there may be two or more small molecule ligands of different types attached to the scaffold (e.g. two different fluorophores; or one type of fluorophore and biotin and/or streptavidin etc.)

The scaffold will conveniently comprise a plurality of groups reactive towards the receiver moiety (which itself will preferably be present or formed in a plurality on the molecule to be labelled).

Typically the scaffold molecule will be in an "activated" state, i.e. have been contacted with an activator reagent, in order to introduce the desired reactive groups, and the scaffold molecule may therefore typically comprise groups which are introduced as a result of reaction with activator reagent such as SMCC and the like.

After attachment of the small molecule ligand(s) and/or activation, the scaffold molecule may be separated from low molecular weight substances, including unreacted SMLs or their hydrolysis products, and exchanged, if required, into a buffer that is more suitable for the subsequent conjugation reactions or for temporary storage or long-term storage of the scaffold. This exchange and/or separation step may be achieved by any of the techniques known to those skilled in the art, the most appropriate of which will normally depend, at least in part, on the scale of the synthesis. The present inventor has found separation using commercially-available desalting columns to be adequate (e.g. Sephadex G-25 "NAP-5" columns or "PD10" columns from GE Healthcare). At a larger scale (>100 mg scaffold), empty glass or polypropylene columns with increased capacity may be packed using hydrated Sephadex G-25, which is available separately as a dry powder.

After attachment of SMLs and/or activation, the scaffold molecule may conveniently be provided frozen or freeze-dried for storage purposes typically in aliquots of about 50 βl up to about 5 mls, preferably about 100 μl to 2 mls. Conveniently the scaffold molecule will be provided as part of a kit, the kit being adapted and designated for use in performing the method of the invention.

A preferred scaffold molecule comprises ovalbumin. The scaffold molecule will preferably comprise a known, pre-determined, average number of attached small molecule ligands. The scaffold molecule may additionally or alternatively comprise a known, pre-determined average number of reactive groups (preferably thiol-reactive groups) per molecule, which can be used to react with receiver moieties on the molecule to be labelled.

Another preferred scaffold molecule is dextran, which can readily be converted into aminated derivatives capable of reacting with AR-SMLs. Moreover, the size of the molecule may be changed as required (dextrans in the range 1000-2,000,000 Daltons are commercially available) providing considerable scope for varying to number of SMLs per scaffold molecule without necessarily changing the density of labelling. This has considerable value with some fluorescent SMLs, which may show quenching (see later) if they are brought into close proximity.

Dextrans used in the present invention are typically 40,000 Daltons or greater. If one assumes that dextrans are spherical, the change in radius/surface area with changing volume (molecular size) may readily be determined using standard mathematical equations. For example, a 2-fold increase in surface area can be achieved by switching from 150 kDa to 450 kDa dextran; the increase in surface area in making the transition from 40 KDa to 500 kDa is 5-fold. Where a single point of attachment to the biomolecule to be labelled is desirable, it is evident from the above considerations that a larger dextran may be used to introduce more SML.

For use in the method of the invention, the scaffold molecule is preferably present in solution, either entirely or partially aqueous, and typically comprising a suitable buffer. In reactions with the SML, the solution is preferably relatively concentrated, at a concentration of at least 10 mgs/ml, more preferably at least 20 mgs/ml, and most preferably at 40 mgs/ml or more.

In a third aspect, the invention provides a kit for use in performing the method of the invention. The kit will comprise a scaffold molecule as defined and/or described previously, and instructions for performing the method of the invention. The kit may preferably comprise a thiol-generator, such as 2-iminothiolane, and/or one or more buffers. One or more of the reagent components of the kit may be provided in freeze-dried form. The kit may optionally comprise one or more of the following: one or more small molecule ligands; one or more activator reagents to activate the scaffold molecule; and one or more molecules to be labelled.

In a fourth aspect the invention provides a conjugate, the conjugate comprising a molecule indirectly labelled, at least one scaffold molecule attached to the molecule indirectly labelled, and at least one small molecule ligand label attached to the scaffold molecule. Advantageously the conjugated is prepared by the method of the first aspect of the invention.

Preferably, but not essentially, the at least one small molecule ligand is covalently attached to the scaffold molecule. Preferably, but not essentially, the scaffold molecule is covalently attached to the molecule indirectly labelled. Preferably the small molecule ligand(s), the scaffold molecule and the molecule indirectly labelled, are all as defined and described as aforesaid. In particular the scaffold molecule preferably comprises ovalbumin or an aminated dextran.

In one embodiment, the invention provides a conjugate comprising a molecule indirectly labelled, said molecule being attached to a plurality of scaffold molecules, each scaffold molecule in turn being attached to at least one small molecule ligand.

In another embodiment the invention provides a conjugate comprising a molecule indirectly labelled, said molecule being attached to a single scaffold molecule, which scaffold molecule is attached to a plurality of small molecule ligands (which may be the same or different).

In preferred embodiments, the small molecule ligands are monovalent with respect to their ability to bind the scaffold molecule.

One feature of the present invention is that a scaffold, (especially a thiol-reactive scaffold), may be synthesised with a pre-determined and pre-optimised amount of attached SML and then attached en bloc to the biomolecule to be labelled. In this way, the method of the invention allows precise control of the ratio of label (or ligand) to molecule to be labelled, the absolute amount of label, and the labelling density and distribution. Advantageously, incorporation of SMLs via a scaffold intermediate is more easily controlled than is direct labelling of the biomolecule with a monovalent reactive SML because (i) the molar ratio of scaffold to biomolecule is relatively low and (ii) steric factors operate to limit the number of scaffold molecules that can physically be attached. This approach to bioconjugation ensures that labelling density is much more predictable and that over-labelling or quenching, in the case of fluorescent SMLs, is easily avoided. ("Quenching" is the phenomenon in which multiple fluorescent moieties are present in close proximity, and interfere with the fluorescence of one another). In most cases there is no need to purify the final conjugate, as the poly-TR scaffold does not have to be used in great excess, since the TR groups are more stable than typical NHS esters and because redundancy of the functional groups means that hydrolysis of TR functions does not necessarily prevent attachment of the scaffold.

The scaffold approach also allows considerable flexibility in conjugate design and optimisation. For example, the attachment of three scaffold molecules, each bearing one SML, to an antibody introduces a total of three SMLs. Equally the attachment of one scaffold molecule bearing three SMLs would introduce the same number of SMLs. However, the conjugates are clearly not equivalent in molecular terms and a performance advantage of particular types of conjugates may be apparent in certain assay situations. Optimisation for a particular application might involve for example, the preparation of three scaffolds with low, intermediate and high density of SML and conjugation with three concentrations of the biomolecule to be labelled, giving nine types of conjugate. The best conjugate is then selected on the basis of performance in a particular immunoassay.

In immunoassays that involve antigen binding followed by a wash step, the presence of small amounts of unconjugated scaffold in an antibody conjugate may be of little significance, as the excess label will be washed away. However, if the presence of unconjugated scaffold is known to be problematic, a molar ratio of antibody/scaffold can be selected to minimise the concentration of free scaffold. A relatively high density of SML per scaffold may also be favoured in these circumstances; subject to any constraints on labelling density that might apply (e.g. the density might be limited by quench effects or the need to accommodate other binding molecules on the scaffold later on).

In the case of scaffolds linked to biotin, a SML frequently used in conjugation reactions, there are two possible applications. In the first, the biotinylated scaffold is conjugated to a binding entity (e.g. an antibody), which then binds non-covalently to an antigen. After washing away excess biotin-scaffold-antibody conjugate, the biotin ligand is used to recruit a streptavidin conjugate incorporating a label that can readily be measured (e.g. HRP). Biotin and streptavidin molecules are commonly used in this way to create bridges that link molecules non-covalently. In this type of assay, any unconjugated biotin-scaffold is removed during the wash steps and cannot have any effect in the final assay.

In the second application, the biotin component of the biotinylated conjugate is used instead to orient the conjugate on a surface to which streptavidin has been attached. In this type of application, small quantities of unconjugated biotin scaffold could compete with biotin-scaffold-antibody conjugate for the immobilised streptavidin, and thus reduce the amount of conjugate captured on the surface. This might be expected to lead to reduced assay sensitivity. However, the methods of the present invention allow conjugates to be prepared quickly and tailored to specific applications generally without the need for wash steps.

The scaffold approach allows the full range of commercially available AR-SMLs, mostly NHS-activated SMLs, to be exploited through the creation of an array of poly-TR scaffolds to which one (or more than one) type of SML has been attached. Since members within any class of reactive SML (e.g. the NHS ester class) all display essentially the same reactivity, the methods of the present invention can be applied to any member within that class. Unlike many AR-SMLs, the TR functions on SML-modified scaffolds are relatively stable and can be stored for long periods in freeze-dried form without concern over loss of active functions.

In a preferred embodiment of the present invention an AR-SML is first reacted with an amine-containing scaffold molecule. In a particularly preferred embodiment an NHS ester derivative of the SML is used. The percentage of a reactive SML that can be incorporated into a scaffold is conveniently estimated by reacting a limiting amount of SML with a concentrated solution of the scaffold molecule, followed by separation into scaffold-bound and free forms by desalting or dialysis. The fact that the rate of decomposition of the SML during storage and rate of hydrolysis in solution are usually unknown is of little concern when one can determine how much SML is required to achieve a particular density of ligand using a relatively inexpensive scaffold molecule.

Preferably, in the case of reactions of scaffolds with NHS esters, a pH of around 7.2 is used to minimise the rate of hydrolysis and the scaffold is used at a relatively high concentration in order to drive the reaction with the NHS ester with amines in the face of competing hydrolysis reactions. For example, the concentration of scaffold is preferably >10 mg/ml, more preferably >20 mg/ml and even more preferably >40 mg/ml. A high concentration of scaffold (i.e. small volume) is also advantageous in that it facilitates subsequent desalting or dialysis steps prior to attachment of the scaffold to the biomolecule of interest.

It will be obvious to anyone skilled in the art that other amine-reactive derivatives (e.g. isothiocyanates, triazines, sulfonyl chlorides, acyl azides, aryl halides, aldehydes, tetrafluorophenyl esters and imidoesters) could also be used, under suitable conditions, instead of NHS derivatives, to effect coupling of SMLs to aminated scaffold molecules. It will also be apparent that TR-SMLs (maleimides, haloacetyl derivatives) could be employed with thiolated scaffolds, and that hydrazide derivatives of SMLs or amine-containing SMLs could be conjugated to aldehydes, as arising, for example, from periodate treatment of dextran or glycoprotein scaffolds.

The total number of accessible amine functions on a scaffold sets an upper limit on the number of AR-SMLs that can be attached. Fluorescent SMLs whose excitation and emission spectra substantially overlap are more likely to suffer from quenching and may need to be incorporated at lower density than those with a larger Stokes' shift. A greater number of fluorescent SMLs can be accommodated without quench effects by increasing the size of the scaffold or by optimising the disposition of the amine functions, since the extent of fluorescence quenching is related to intermolecular distance (i.e. the closer the fluorophores the more likely that quenching will occur). While smaller scaffolds may be able to accommodate fewer fluorophores than larger scaffolds, it may be possible to attach a greater number of smaller scaffolds to a biomolecule without compromising biological activity.

Only a proportion of the amines (or other possible points of attachment) are utilised in the reaction with SMLs to ensure that sufficient groups remain to allow the attachment of TR functions. Thus the total number of available amines is an important consideration when selecting or designing a suitable scaffold. If the total number of amines on a scaffold is insufficient for a particular application either a different scaffold can be selected or chemical modification reactions on the scaffold can be performed to alter the number or types of reactive centres. In the case of dextrans, chemistry that has already been developed can simply be applied to a larger molecule.

Methods for introducing new functional groups are comprehensively described in the scientific literature. Carboxyl functions, if present on the scaffold, can be conjugated with amine containing molecules in the presence of a carbodiimide. Condensation with diamines (or polyamines) introduces new surface amines, which provide potential sites for coupling to AR-SMLs. Suitable diamines include, but are not limited to, ethylene diamine and 2,2-(ethylenedioxy)bis (ethylamine) [EDBA].

Carboxymethyl dextran provides a convenient starting point for the introduction of amine functionality using diamines. A combination of a diamine and a monoamine provides a convenient way of simultaneously introducing surface amines and modifying the properties of the dextran. The monoamine may be exploited to control the total number of amines and/or to provide other surface features (e.g. polar, hydrophobic or charged groups). For example, carbodiimide-mediated condensation with ethanolamine introduces a polar relatively unreactive hydroxyl group and eliminates one negative charge for each molecule attached. Similarly, glycinamide, agmatine and taurine may be used to introduce amide (neutral), guanidino (positively charged) and sulphonic acid (negatively charged) moieties, respectively, via carbodiimide-mediated condensation. Similarly, glycinamide, agmatine and taurine may be used to introduce amide (neutral), guanidine (positively charged) and sulphonic acid (negatively charged) moieties, respectively, via carbodiimide-mediated condensation. Such introductions may be used to reduce non-specific binding of conjugates or to change the environment in which the immobilised SML is situated, for example, to influence/enhance the fluorescence properties of fluorescent SMLs.

Carboxylic acid functions can also be exploited to introduce thiol functions for subsequent reaction with TR-SMLs (e.g. iodoacetamido derivatives). Carbodimide-mediated reaction of an excess of cystamine with the scaffold introduces protected thiols that can be released by treatment with DTT or other reducing agents. One possible advantage of exploiting carboxyls in this way is that amine functions on the scaffold are still available for other reactions. This approach might be useful if the total number of amines is limited and/or if the reactive SML is available only as a TR derivative. Any excess thiols are capped with monomaleimides or are exploited to introduce TR functions using homobifunctional TR crosslinkers (e.g. bismaleimidohexane)(BMH).

Amine groups can also be exploited to introduce thiols, assuming that this operation leaves sufficient amine groups to complete the construction of the scaffold through the introduction of e.g. TR functions later on. For example, amines can be reacted with 2-iminothiolane to generate free thiols, or with N-succinimdyl-S-acetylthioacetate (SATA) or N-succinimdyl-S-acetylthioacetate (SATP) to generate protected thiols that can be released with hydroxylamine, or with N-succinimidyl 3-(2-pyridyldithio)propionate (SPDP) which releases a thiol upon treatment with a reducing agent, such as dithiothreitol. If the scaffold has aldehydye functions, 2-acetamido-4-mercaptobutyric acid hydrazide can be used to introduce the required thiols.

If the scaffold has too many amines, a reaction with a limiting amount of acetic anhydride or NHS-acetate can be used to block irreversibly a proportion of these groups. Succinic anhydride and glutaric anhydride also eliminate amine functions and introduce one carboxyl function for each amine modified. A reversible block of excess amines can be achieved with maleic anhydride or citraconic anhydride.

Thus chemical modification reactions can be used to introduce new reactive centres and/or to alter the physicochemical properties of scaffolds and conjugates prepared from them, for example, to improve assay signals and to try to minimise non-specific interactions.

Once the SML has been reacted with the scaffold the crude mixture, preferably without purification, may be reacted with another molecule (an "activator") that introduces the group or groups (e.g. thiol-reactive groups) which are reactive towards a receiver moiety present on the molecule to be labelled. An advantage of using NHS chemistry to introduce the SML is that the same buffer conditions can then be used to introduce thiol-reactive functions by means of heterobifunctional reagents that are capable of reacting at one end with amines (via an NHS ester) and at the other with thiols. Many such reagents have NHS moieties, such as succinimidyl-4-(N-maleimidomethyl)cyclohexane-1-carboxylate [SMCC] which is particularly preferred as the maleimide function is stabilised by the adjacent aliphatic ring. Other reagents with similar chemical reactivity include MBS (m-maleimidobenzoyl-N-hydroxysuccinimide ester); SIAB [succinimidyl(4-iodoacetyl)aminobenzoate]; GMB S [N-(γ-maleimidobutyryloxy)succinimide ester]; SIAX [succinimidyl 6-((iodoacetyl)amino)hexanoate; and SLAC [succinimidyl 4-(((iodoacetyl)amino)methyl) cyclohexane-1-carboxylate. In some cases sulfonated analogues are also available (e.g. sulfo-SMCC) which show greater solubility in aqueous solution than the non-sulfonated forms.

Under the conditions employed for the preparation of the scaffold, and in the absence of thiols, the NHS moiety of the heterobifunctional reagent selectively reacts with amines and the TR functions become displayed on the surface of the scaffold. The resulting poly-TR SML-scaffold combination is purified preferably by desalting or by dialysis and either used immediately or freeze-dried preferably in combination with 2-IT and optionally with other suitable excipients so that high efficiency single-step conjugations to biomolecules can be performed using methods detailed in WO 2007/068906.

If the attachment of the SML does not involve the use of an NHS ester it may be necessary to desalt or dialyse the SML-scaffold before attachment of the thiol-reactive functions. This is because a higher pH is required for reactions with most other amine-reactive groups. Isothiocyanates, for example, react most efficiently at pH values around 9.0. This is not ideal for the introduction of TR functions using most heterobifunctional reagents as the 'thiol-reactive' group may also react with amines at high pH values or decay quite rapidly. However, an advantage of the present invention is that desalting and dialysis steps are simple because of the high concentration/small volume of samples, thus different chemistries can be used for attachment of the SML and the TR functions as long as samples are exchanged into a suitable buffer at each stage.

Irrespective of how the poly-TR SML scaffold is constructed it may be necessary, depending on the final application, to quench excess reactive groups before the conjugate is used. WO 2007/068906 describes several quench strategies that can be used with polypeptide labels (e.g HRP, phycoerythrin). Glycine, for example, is used to attack 2-iminothiolane and thus halt further thiolation of either the biomolecule to be labelled or other biomolecules that may be present when the conjugate is used. A secondary effect is that low molecular weight thiols so released can also deactivate TR functions. In the present invention two unexpected observations suggested that a different approach might be preferred in the case of dye-labelled dextran scaffolds. First, a high level of SMCC modification, which is greatly preferred for the in situ thiolation approach described in WO 2007/068906, was found to be associated with a significant reduction in the fluorescence of fluoresceinylated dextran scaffolds. Second, the use of mercaptoethanol to block unwanted reactivity of poly-maleimido fluoresceinylated dextran/antibody conjugates with thiolated surfaces was found to increase the fluorescence associated with specific binding of the antibody to its antigen. The action of the blocking thiol in enhancing fluorescence was shown in separate tests to be a direct effect on the scaffold, the thiol apparently relieving the quenching effect on the fluorescent dye of the maleimide functions derived from SMCC. The quenching effect was reduced by a reduction in ionic strength of the solution (e.g. dilution into water) and by addition of 10% DMSO, suggesting that quenching is due, at least in part, to hydrophobic interactions.

In the present invention, a combination of glycine and a thiol is preferred for halting conjugation reactions. In a particularly preferred embodiment, the pH of the combined reagent is sufficiently low to preserve thiols (i.e. by preventing oxidation to the disulfide) and the buffering capacity is sufficiently low that when the solution is added to the conjugation mixture the near neutral pH of the conjugation mixture is maintained, thus providing favourable conditions for blocking TR functions and deactivating excess 2-iminothiolane. A particularly preferred formulation is 50 mM glycine, pH 2.3 containing around 10 mM thiol, which is added to give final concentrations of glycine and thiol of around 5 mM and 1 mM, respectively. A large number of thiols were found to enhance by 60-100% the fluorescence of poly-maleimido fluoresceinylated scaffolds, including dithiothreitol, mercaptoethylamine, mercaptoethanol, mercaptopropionic acid, L-cysteine and mercaptosuccinic acid. Thiols that also incorporated carboxylic acid groups were particularly effective; mercaptosuccinic acid gave the greatest enhancement.

The invention will now be further described by way of illustrative example and with reference to the accompanying drawings, in which:

FIG. 1 is a schematic diagram to show the key steps of the method of the invention. In the first stage (i), a scaffold with a plurality of functional groups (X and, optionally, W) is contacted with a limiting amount of the SML to form a covalent bond between some X functions and SML. Typically X is an amine group. W is a group that can be converted into X if required, or used in some other way, or not exploited at all. In step (ii) the scaffold-SML molecule is contacted with a bifunctional reagent (BFR), typically a heterobifunctional reagent, which has X-reactive and thiol reactive (TR) functions and converts X functions into TR functions. In the final step (iii), the poly-TR scaffold-SML molecule, a thiol generator (typically 2-iminothiolane; 2-IT) and the biomolecule to be labelled (e.g an antibody; Ab) are brought into simultaneous contact with one another. The thiol generator acts upon the biomolecule to be labelled and converts amine functions into highly nucleophilic thiols, which immediately react with the poly-TR scaffold to create a link between the antibody and the scaffold (and thus an indirect link between the antibody and the SML) by means of a single step conjugation reaction. Excess reactive groups automatically decay though this can be accelerated by means of a suitable quencher, according to methods described in WO 2007/068906.

EXAMPLES

Example 1

Preparation of
Poly-Maleimido-Fluoresceinylated-OVA

Ovalbumin (OVA) (A5505; lot 076K7045) at 40 mg/ml (approx 0.87 mM; 1 ml) in 100 mM sodium phosphate pH 7.2 was reacted with a limiting amount (with respect to ovalbumin amines; 20 lysines per molecule, 16 of which are normally accessible; Battra P P, Int J Biochem. 23, 1375-84, 1991) of 100 µl of 22.5 mM 5-(and 6-)carboxyfluorescein succinimidyl ester (Molecular Probes C1311; lot 25547W) dissolved in DMSO. After 30 minutes at 25° C. in the dark a further addition of 50 µl of sulfo-succinimidy1-4-(N-maleimidomethyl)cyclohexane-1-carboxylate (sSMCC) was made from 200 mM stock in DMSO to give final concentrations of sSMCC and ovalbumin of 8.7 mM and approx 0.76 mM respectively. After a further 30 minutes of incubation in the dark the sample of poly-maleimido-fluoresceinylated-OVA was desalted on Sephadex G-25 (PD10 columns; GE Healthcare) into 10 mM sodium phosphate pH 5.8. A 125 µl aliquot was diluted with 775 µl of sodium phosphate buffer pH 5.8 and 100 µl of 33% trehalose stock (prepared from 1 g trehalose plus 2 ml water). Aliquots (1000; 250 µg) of the trehalose/poly-maleimido-fluoresceinylated-OVA mixture were snap frozen on liquid nitrogen and freeze dried according to methods described in WO 2007/068906.

Example 2

Preparation of Coated Plates 96-well Maxisorp plates (Nunc) were coated with 50 μl/well of purified IgGs (20 μg/ml) or streptavidin (5 μg/ml) for at least 16 hours at 4° C. Before use, coated plates were washed 5 times with 50 mM Tris/150 mM NaCl, pH 8.0 (TBS) and blocked for 30-60 min with 0.1% BSA in TBS (blocker). Blocked plates were washed 5 times with TBS prior to incubation with conjugates diluted, as required, in blocker.

Example 3

Conjugation of Goat Anti-Rabbit IgG with Poly-Maleimido-Fluoresceinylated-Ovalbumin 50 μl of goat anti-rabbit IgG (1 mg/ml) in 200 mM Hepes/1 mM EDTA, pH 7.5, was mixed with 5 μl 10 mg/ml poly-maleimido-fluoresceinylated-OVA (after resuspension of the material from Example 1 in 25 μl of water). Four 11 μl portions of the mixture were incubated with 1 μl of 2-iminothiolane (varying concentrations: 8 mM, 4 mM, 2 mM and 0 μmM) giving final concentrations of 667 μM, 333 μM, 167 μM and 0 μM. After incubation overnight at 25° C., the samples were diluted 1/100 in 50 mM Tris/150 mM NaCl/0.1% BSA (blocker) and incubated for 1 hour at 25° C. on a 96-well Maxisorp microtitre plate coated with rabbit IgG (Example 2). After washing 5× with TBS, 100 μl of TBS was added to each well prior to reading (1 sec per well) on a Wallac Victor using excitation/emission settings of 485/535 nm and CW lamp energy setting of 11720.

Figure 1:
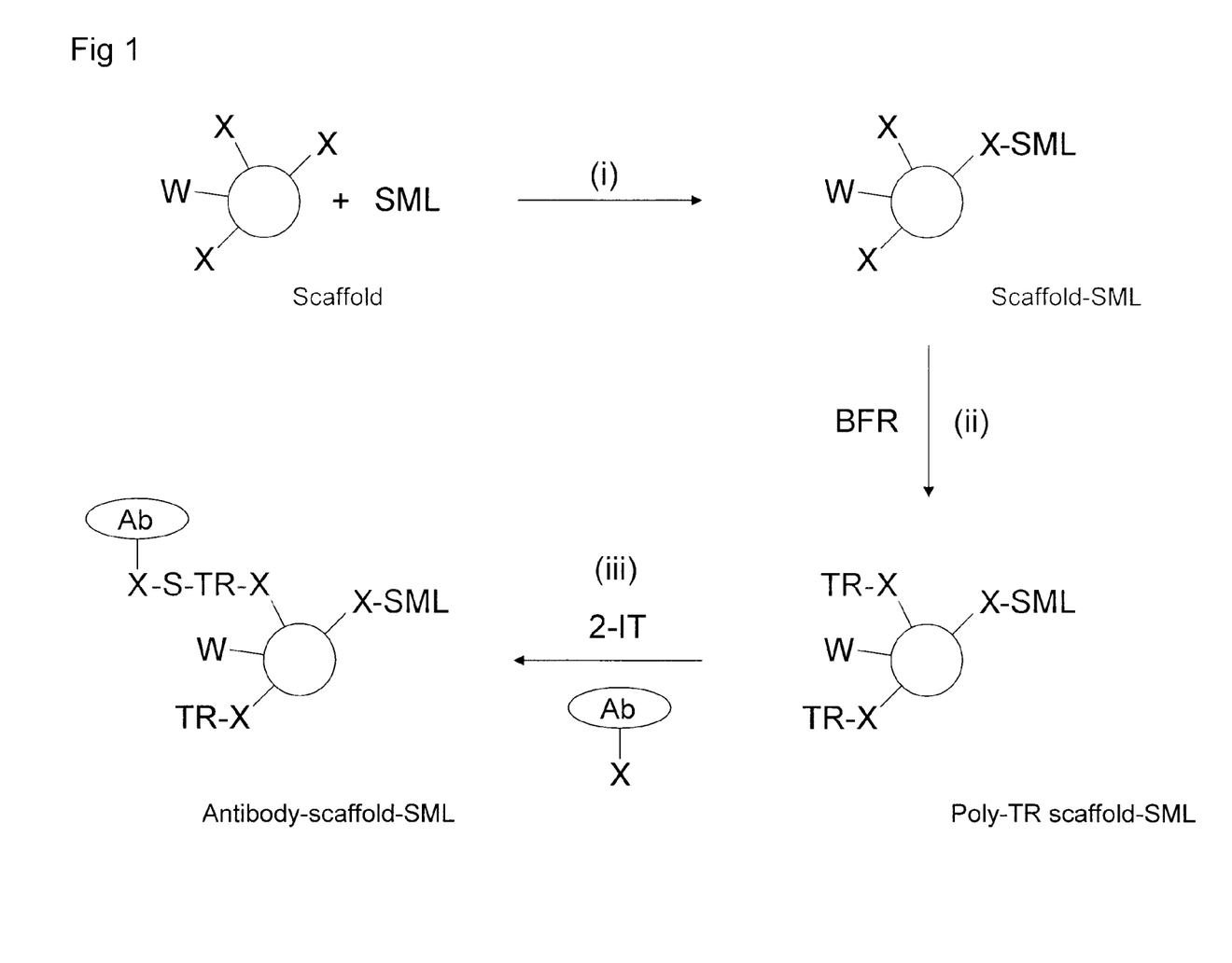
Figure 2:
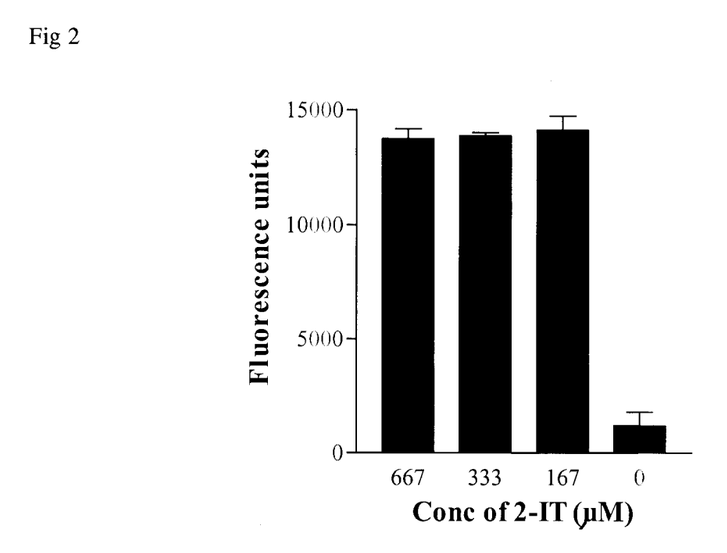
FIG. 2 is a bar chart showing the amount of fluorescence detected (in arbitary fluorescence units) in an assay using a conjugate prepared using various amounts of a "thiol-generator", 2-iminothiolane.

The data are shown in FIG. 2. As can be seen, the lowest concentration of 2-IT tested was as efficient as the highest concentration. In separate experiments, it was found that even very high concentrations of 2-IT (8 mM final concentration) were still effective, though a slight reduction in conjugation efficiency was observed compared with that for 800 μM 2-IT (data not shown) possibly because of contaminating thiols in the 2-IT preparation and/or excessive modification of amines. Thus 2-IT may be used over a broad range of concentrations. In the absence of 2-IT the conjugation efficiency was low, because in the absence of thiols the antibody reacts only slowly (via amines) with the TR functions on the scaffold.

Example 4

Production of Poly-Maleimido-Biotin-Ovalbumin Scaffold

Ovalbumin (A5505; lot 076K7045) at 40 mg/ml (approx 0.87 mM; 125 μl; 5 mg) in 100 mM sodium phosphate pH 7.2 was reacted with 6.25 μl of 60 mM NHS-LC-biotin (Pierce 21335) in DMSO. After 1 hour at 25° C., 14 μl of sulfo-succinimidyl-4-(N-maleimidomethyl)cyclohexane-1-carboxylate (sSMCC) was added from 200 mM stock in DMSO to give final concentrations of sSMCC and ovalbumin of 19.3 mM and approx 0.75 mM respectively. After 1 hour at 25° C. the sample of poly-maleimido-biotinylated-ovalbumin was desalted on Sephadex G-25 (NAP-5 columns; GE Healthcare) into 300 μl of 10 mM sodium phosphate pH 5.8. The sample was diluted with 60 μl of sodium phosphate buffer pH 5.8 and 40 μl of 33% trehalose stock (prepared from 1 g trehalose plus 2 ml water). Aliquots (10 μl; 125 μg) of the trehalose/poly-maleimido-fluoresceinylated-OVA mixture were snap frozen on liquid nitrogen.

Example 5

Optimising the Ratio of Antibody to Scaffold

Figure 3:
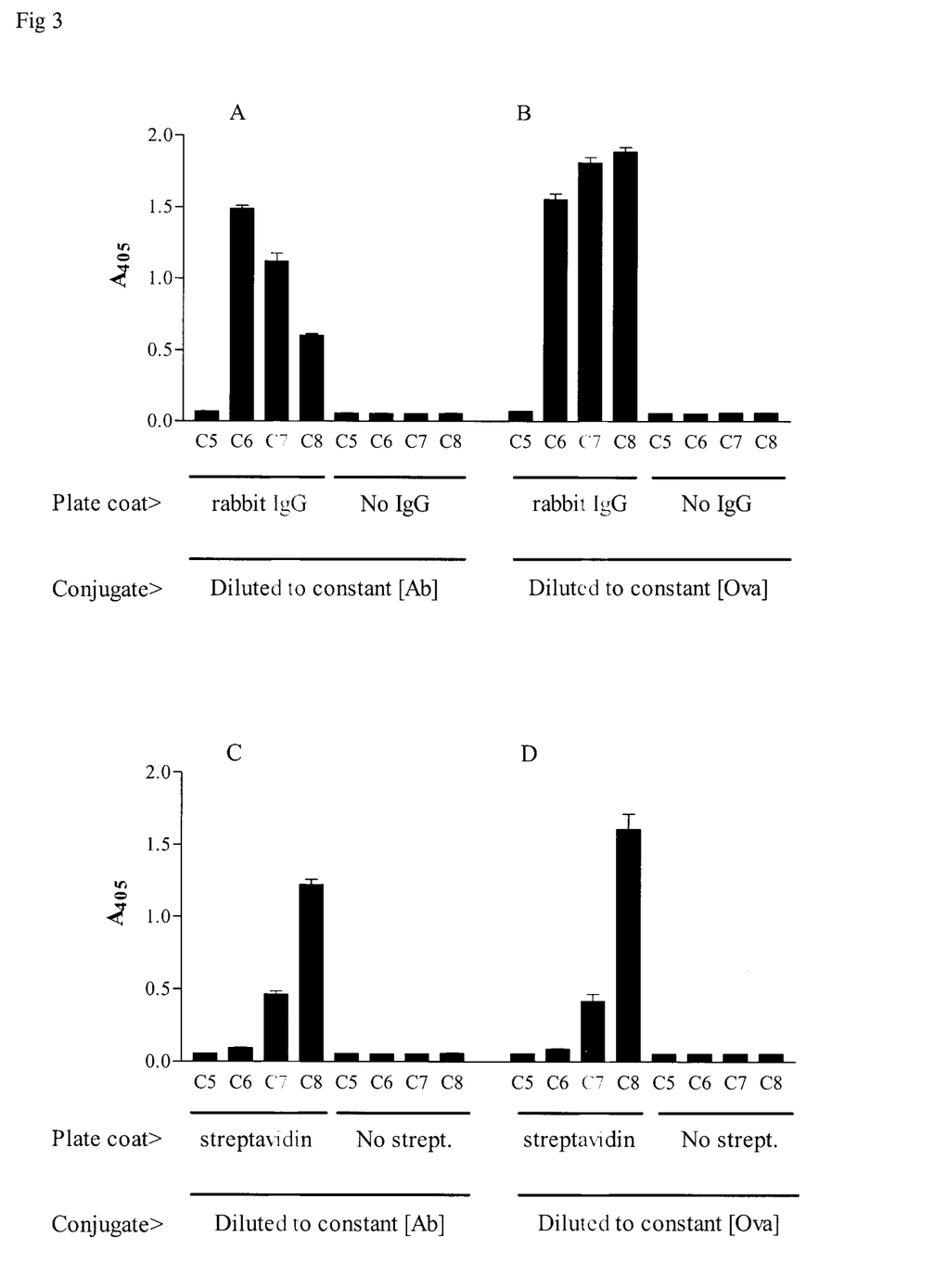
FIG. 3 shows four bar charts (A-D): panels A & B show the absorbance (at 405 nm) measured in an ELISA using rabbit IgG-coated microtitre plates and a conjugate comprising goat anti-rabbit IgG labelled indirectly with biotin, coupled via an intervening ovalbumin scaffold; panels C & D show absorbance (at 405 nm) measured in an assay using the same conjugate captured on streptavidin-coated plates. For panels A & C, the assay was performed using a constant antibody concentration, whilst for panels B & D, the assay was performed using a constant concentration of scaffold. C6-C8 represent conjugates formed using different IgG: ovalbumin ratios, and C5 represents a control conjugate (no IgG)

Aliquots (10 μl) of poly-maleimido-biotin-ovalbumin scaffold (Example 4) were incubated overnight at 25° C. in a final volume of 50 μl (made up with water as required) with 5 μl of 2M Hepes/10 mM EDTA, pH 7.5, 5 μl of 1.1 mg/ml 2-IT (8 mM stock) and varying amounts (5 μl, 10 μl or 20 μl; 55 μg, 110 μg or 220 μg) of goat anti-rabbit IgG (11 mg/ml), giving molar ratios (scaffold:Ab) (assuming Ab mol weight of 150, 000 and scaffold mol weight of ~50,000) of 6.8:1 (conjugate 6; C6) 3.42:1 (C7) and 1.7:1 (C8). A control conjugation with no antibody was also set up (C5). A portion of each conjugate was diluted 1/10,000 in blocker (i.e. to give constant scaffold concentration) and another set of dilutions was prepared to give a fixed antibody concentration of 0.1 μl/ml (1/10,000 dilution or greater, depending on the conjugate). Samples were tested in two assays (i) an ELISA using rabbit IgG plates. After incubation with conjugates for 1 hour at 25° C. the plate was washed with TBS and wells were incubated for 1 hour at 25° C. with 1/2,500 streptavidin-HRP (Innova Biosciences #857-0005). After washing, HRP was detected using ABTS reagent (1 mM ABTS in 50 mM sodium acetate, pH 5.0, containing 1 μl of $H_2O_2$ per ml of reagent. (ii) a capture assay using a steptavidin plate. After incubation with conjugates for 1 hour at 25° C. the plate was washed with TBS and wells were incubated for 1 hour at 25° C. with protein A HRP. After washing, protein A-HRP that was bound to the captured goat antibody-scaffold conjugate was detected using ABTS substrate. The results are shown in FIG. 3.

As can be seen in panel A, in the rabbit IgG ELISA the highest ratio of scaffold to antibody gives the greatest signal when conjugates are diluted to a fixed concentration of antibody. The relatively modest signal for conjugate 8 (C8) on rabbit IgG coated wells presumably arises because fewer scaffold units are attached per antibody molecule. Binding to control wells (no coated IgG) is low in all cases. In panel B, with fixed scaffold concentration, the higher concentration of antibody in C8 compared with C7 and C6 more than compensates for the lower number of scaffold units per antibody molecule and all three conjugates give relatively high absorbance values. In the streptavidin capture assay with fixed antibody concentration (panel C), the trend is reversed compared with that seen in panel A. This observation is most likely explained as one progresses from conjugate C8 to C6 by (i) increasing amounts of free scaffold, which might compete with the antibody conjugate for binding to immobilised streptavidin, and (ii) increasing number of scaffold units per antibody, which might prevent the binding interaction of the Fc antibody domain with protein A-HRP. However, since C6 binds effectively to immobilised rabbit IgG (panel A)(though not via the Fc region), it is more likely that the level of free biotinylated scaffold explains the low binding of C6 to the streptavidin plate; indeed, SDS gels of the three conjugates (data not shown) revealed significant levels of free scaffold in C6 where the ratio of scaffold to antibody was relatively high. Since the capture of scaffold-antibody conjugates on streptavidin surfaces requires only one scaffold and one favourably oriented biotin molecule a low molar ratio of scaffold to antibody is preferred in this type of application. On the other hand, if the biotinylated scaffold is used to capture a streptavidin-based detection reagent, a relatively high molar ratio of scaffold to antibody may be preferred in order to increase assay sensitivity and, in this situation, any unconjugated scaffold is simply washed away. These data illustrate that conjugate performance is dependent on assay configuration and that simple variation of molar ratios can be used to optimise performance and to generate conjugates without the need for further purification.

Example 6

Optimising Density of Biotin on an Ovalbumin Scaffold

Aliquots of ovalbumin (A5505; lot 076K7045) at 40 mg/ml (approx 0.87 mM; 125 µl; 5 mg) in 100 mM sodium phosphate pH 7.2 were each mixed with 12.5 µl of one of three solutions of NHS-LC-biotin (Pierce 21335)(10 mM, 30 mM or 60 mM) in DMSO or with DMSO alone (control scaffold). After 1 hour at 25° C., 13.5 µl of sulfo-succinimidyl-4-(N-maleimidomethyl)cyclohexane-1-carboxylate (sSMCC) was added from 200 mM stock in DMSO to give final concentrations of sSMCC and ovalbumin of 17.9 mM and approx 0.72 mM respectively. After 1 hour at 25° C. the samples (151 µl) were desalted on Sephadex G-25 (NAP-5 columns; GE Healthcare) into 400 µl of 10 mM sodium phosphate pH 5.8, and made up to 500 µl with 50 µl of sodium phosphate buffer, pH 5.8, and 50 µl of 33% trehalose stock (prepared from 1 g trehalose plus 2 ml water). 5 µl aliquots of each type of scaffold were mixed with 5 µl of goat anti-rabbit IgG (10 mg/ml), 2 µl of 2M Hepes/10 mM EDTA, pH 7.5, 6 µl of water and lastly 2 µl of 2-IT (8 mM). After overnight incubation at 25° C., conjugates were incubated for 1 hour at 25° C. on a rabbit IgG plate (Example 2). After washing, wells were incubated with 1/10,000 streptavidin HRP for 1 hour at 25° C. and then washed before detection of HRP with ABTS substrate according to Example 5.

Figure 4:
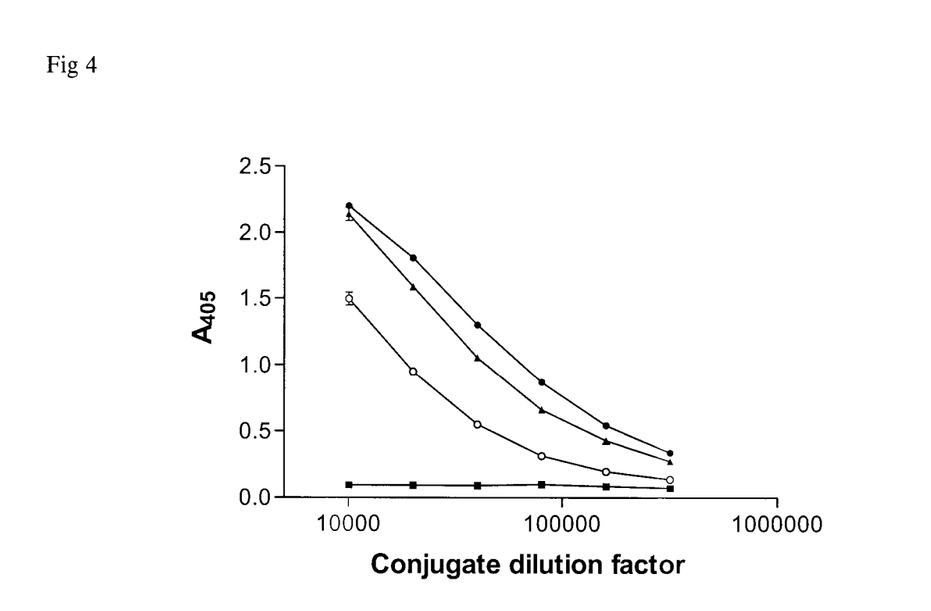
FIG. 4 is a graph showing absorbance (at 405 nm) measured in an ELISA using a rabbit IgG-coated plates and a conjugate comprising goat anti-rabbit IgG labelled indirectly with biotin via an intervening ovalbumin scaffold. Conjugates were prepared using different concentrations of biotin (open circles—1 mM; triangles—3 mM; solid circles—6 mM; solid squares—no biotin) and tested at a range of dilutions.

As can be seen in FIG. 4, in the absence of biotin on the scaffold (squares) only background binding is seen. Conjugates prepared from scaffolds prepared with 1 mM (open circles), 3 mM (triangles) or 6 mM biotin NHS ester (solid circles) all show significant binding at 1/10,000 conjugate dilution but the conjugate prepared with 6 mM biotin gave the highest absorbance values, presumably because it was able to capture more streptavidin HRP than the other conjugates.

Example 7

Optimising the Amount of sSMCC

Four aliquots of ovalbumin (A5505; lot 076K7045) at 40 mg/ml (approx 0.87 mM; 125 µl; 5 mg) in 100 mM sodium phosphate pH 7.2 were each reacted with 12.5 µl of 60 mM NHS-LC-biotin (Pierce 21335) in DMSO. After 1 hour at 25° C., samples were reacted with 13.5 µl of one of three concentrations (200 mM, 100 mM or 50 mM) of sulfo-succinimidyl-4-(N-maleimidomethyl)cyclohexane-1-carboxylate (sSMCC) in DMSO or with DMSO alone to give final concentrations of sSMCC of approx 17.9 mM, 8.9 mM 4.5 mM and 0 mM, respectively. After 1 hour at 25° C. the samples (151 µl) were desalted on Sephadex G-25 (NAP-5 columns; GE Healthcare) into 400 µl of 10 mM sodium phosphate pH 5.8, and made up to 500 µl with 50 µl of sodium phosphate buffer, pH 5.8, and 50 µl of 33% trehalose stock (prepared from 1 g trehalose plus 2 ml water). Conjugates were set up and analysed by ELISA exactly as described in Example 6.

Figure 5:
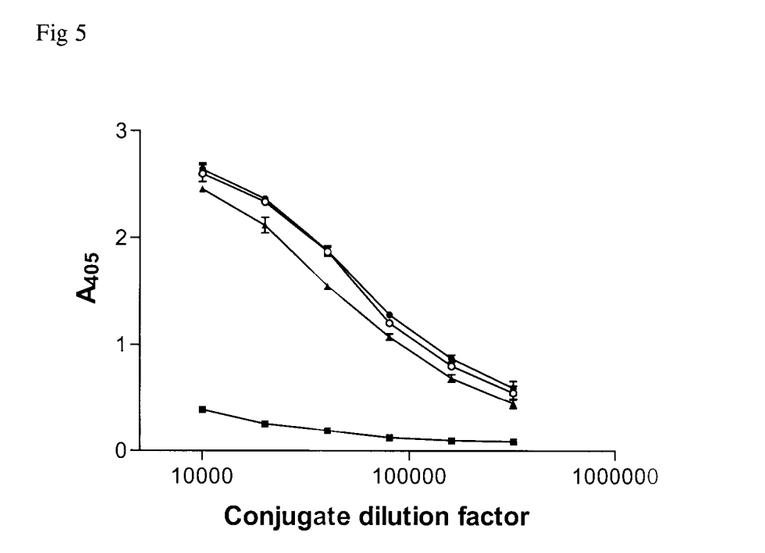
FIG. 5 is a graph showing absorbance (at 405 nm) in an experiment similar to that depicted in FIG. 4, except here testing conjugates prepared using different concentrations of activator reagent (zero—solid squares; triangles—5 mM; open circles—10 mM; solid circles—20 mM).

As can be seen in FIG. 5, relatively low absorbance values were seen for antibody conjugate prepared from scaffold lacking sSMCC (squares). A sSMCC concentration of at least 10 mM (open circles) was required to achieve near maximal absorbance values. This concentration gave significantly higher values than 5 mM sSMCC (triangles), and values similar to those obtained with 20 mM sSMCC (solid circles).

Example 8

Preparation of Scaffolds with Isothiocyanate SMLs

Ovalbumin at 40 mg/ml in sodium bicarbonate pH 9.2 was reacted with 2.5 mM fluorescein isothiocyanate (from 25 mM stock in DMSO) for 3 hours at 25° C. in the dark. The sample was buffer exchanged by desalting into 100 mM sodium phosphate pH 7.2 and adjusted to 20 mg/ml. sSMCC was added to a final concentration of 10 mM from a 200 mM stock in DMSO. After further incubation for 1 hour at 25° C. the sample was desalted into 10 mM sodium phosphate buffer pH 5.8.

Example 9

Production of Aminated Dextran Scaffolds

9A. Via aldehyde derivative. Dextran (80 mg/ml in water; 0.5 ml) with a molecular weight of 80,000 (i.e. 1 mM concentration) was reacted with 100 µl of 500 mM sodium periodate for 1 hour at 25° C. in the dark. The activated dextran (0.6 ml) was desalted on Sephadex G25 (PD10 column) into 0.15M sodium chloride (1.3 ml final volume). 150 µl of sodium bicarbonate/10% (v/v) 2,2-(ethylenedioxy)bis(ethylamine) [EDBA] pH 9.2 was added. After 30 min at 25° C., the resulting Schiff's bases were reduced with 50 mM sodium borohydride (from 5M stock in 1M NaOH). After 30 min the aminated dextran was desalted into 0.15M NaCl using a PD10 column and 0.5 ml fractions were collected. The early eluting high molecular weight material that was amine positive (using the TNBS test; Bioconjugates techniques, GT Hermanson ISBN 0-12-342336-8, p112) was pooled. Amine content of the pool was ~25 mol amine per mol of dextran.

9B. via carboxymethyl (CM) derivative. 5 g of Dextran (150 kDa or 400-500 kDa) was added to a freshly prepared solution of 50 ml 1M bromoacetic acid/2M NaOH and vigorously shaken for 1 min and then subjected to gentle mixing at 25° C. for 24 hours. CM dextran was desalted on Sephadex G-25 columns into 50 mM MES, pH 6.0 (adjusted with NaOH). To 10 ml of CM-dextran (~67 mg/ml) in 50 mM MES pH 6.0 was added 2 ml of 0.5M MES/2M ethylene diamine, pH 6.0 and 1.3 ml of 1M EDC [1-ethyl-3-(3-dimethylaminopropyl)carbodiimide hydrochloride]. The reaction was allowed to proceed for 16 hours at 25° C. and the resulting aminated dextran was desalted on Sephadex G-25 into 0.1M sodium phosphate pH 7.2. Amine substitution was ~17 mol per mol of 150 kDa dextran and >61 mol per mol of 400-500 kDa dextran.

Example 10

Modification of Carboxyl Functions to Introduce Extra Amines to Ovalbumin Scaffold 375 µl of ovalbumin (40 mg/ml) in 50 mM MES, pH 6.0, was added to 300 µl of 1M EDBA in 50 mM MES, pH 6. 75 µl of EDC was added in 50mM MES pH 6 buffer. By using excess diamine (EDBA) to prevent crosslinking of ovalbumin, the degree of conversion of carboxyls (and thus incorporation of amines) is controlled by limiting the amount of EDC. Stock concentrations of 100 mM, 20 mM and 4 mM EDC (and 0 mM for controls)(final concentrations of 10, 2, 0.4 and 0 mM, respectively) were used. Higher stock concentrations (500 mM or 1M EDC) introduced very large numbers of amines but provided aminated scaffolds that precipitated when further reacted with sSMCC. Aminated scaffolds were desalted on PD10 columns equilibrated in 0.15M NaCl to remove excess diamine, EDC and reaction by-products. The final volume of the desalted sample was 1.25 ml. Assessment of amine content using TNBS reagent showed that treatment with 10, 2 and 0.4 mM EDC in the presence of excess diamine introduced around 6, 1 and 0 new amine groups per scaffold molecule, respectively.

Example 11

Production of Thiolated Ovalbumin Scaffold for Reaction with Iodoacetamido Biotin Reactions were set up exactly as described in Example 10 except that the diamine EDBA was replaced with cystamine. After overnight incubation at 25° C., samples were desalted on Sephadex G25 into 100 mM sodium phosphate pH 8. 125 µl of 40 mg/ml DTT was added and after incubation at room temperature for 30 min the sample was desalted into 100 mM sodium phosphate pH 7.2. The thiolated samples were immediately reacted with a 2-3 fold molar excess (with respect to thiols) of iodoacetyl-LC biotin (Pierce 21333, lot DG56028) for 3 hours in the dark at 25° C., desalted into 100 mM sodium phosphate pH 7.2, and then further processed as described for other scaffold-SML molecules (e.g. Example 7).

Example 12

Production of Poly-Iodoacetyl Fluoresceinylated Dextran (40 kDa) Scaffold

Amino-dextran of molecular weight 40,000 (9.3 mol amine per mol) (Molecular Probes, D1861) (40 mg/ml; 1 mM) in 100 mM sodium phosphate pH 7.2 was reacted for 16 hours at 25° C. in the dark with 100 µl of 10 mM 5-(and 6-)carboxyfluorescein succinimidyl ester (Molecular Probes C1311; lot 25547W) dissolved in DMSO. 200 µl of the scaffold was further reacted with 20 µl of 200 mM iodoacetic acid NHS ester in DMSO for 1 hour at 25° C. in the dark. The 220 µl sample was desalted on a NAP-5 column into 450 µl of 10 mM sodium phosphate pH 5.8 and made up to 500 µl with 33% trehalosestock (prepared from 1 g trehalose plus 2 ml water). Conjugation with goat-anti-rabbit IgG (5 mg/ml) was carried out by combining, in the following order, 8 µl of water, 6 µl of a scaffold/buffer mixture [4 µl of scaffold+2 µl of 2M Hepes/10 mM EDTA, pH 7.5], 4 µl of IgG and 2 µl of 8 mM 2-iminothiolane, and reacting overnight at 25° C. in the dark.

Example 13

Comparison of Conjugates Prepared with 150 kDa and 400-500 kDa Poly-Maleimido Fluoresceinylated Dextrans. Fluorescence Signals on Control Wells were Low for all Four Conjugates (bars E, F, G & H)

Aminated dextrans (prepared as described in Example 9B) (0.25 ml) were reacted with 5-(and 6-)carboxyfluorescein succinimidyl ester (4.5 µl of 100 mM stock in DMSO)(~1.8 mM final concentration). After 1 hour at 25° C. sulfo-SMCC was added (7.5 µl of 200 mM stock in DMSO)(~6 mM final concentration). The poly-maleimido fluoresceinylated dextrans (150 kDa and 400-500 kDa) were desalted on Sephadex G25 columns (PD10, GE Healthcare) into 10 mM sodium phosphate pH 5.8 (1.5 ml elution volume). Further additions of 2.55 ml water, 0.45 ml trehalose (1 g+2 ml water) and 22.5 µl 2-iminothiolane (80 mM stock; ~400 µM final concentration) were made. Aliquots (40 µl) of each poly-maleimido fluoresceinylated dextran (~2.5mg detran/ml) were freeze-dried.

Goat anti-rabbit IgG (21.6 mg/ml) was diluted to 2.5 mg/ml (stock X) using a diluent prepared by mixing 1 part 2M Hepes/10 mM EDTA, pH 7.5, and 9 parts water. Further 1 in 3 dilutions of stock X were prepared to give solutions of 0.8325 mg/ml (stock Y) and 0.277 mg/ml (stock Z). Vials of the freeze-dried poly-maleimido fluoresceinylated 150 kDa dextran were reconstituted with 40 µl of either antibody stock X (i.e. 100 µg antibody; 1:1 Ab:dextran ratio) or stock Y (i.e. 33.3 µg antibody; 1:3 Ab:dextran ratio). Vials of the freeze-dried poly-maleimido fluoresceinylated 400-500 kDa dextran were reconstituted with 40 µl of either antibody stock Y (i.e. 33 µg antibody; 1:1 Ab:dextran ratio) or stock Z (i.e. 11.1 µg antibody; 1:3 Ab:dextran ratio. After 5 hours, conjugates were diluted with appropriate volumes of TBS/0.1% BSA to normalise the concentrations with respect to antibody to 4 µg/ml.

Figure 6:
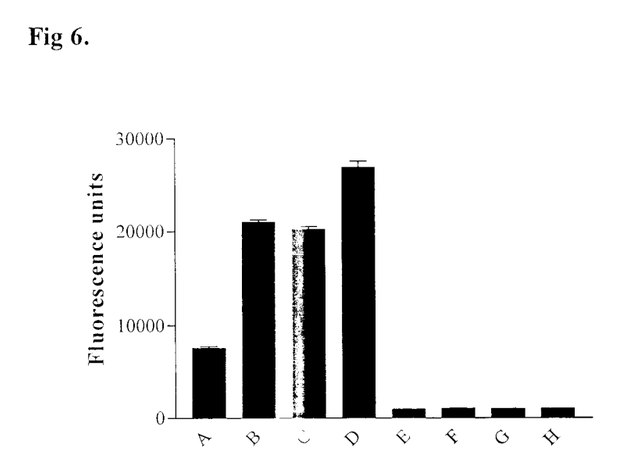
FIG. 6 is a graph showing fluorescence units obtained with various goat anti-rabbit conjugates prepared with fixed amounts (100 µg) of two poly-maleimido fluoresceinylated dextrans (150 kDa and 400-500 kDa) when assayed using black polystyrene plates coated with rabbit IgG (A-D) or without rabbit IgG (E-F). A, C, E and G show data for the 150 kDa dextran scaffold, and B, D, F and H for the 400-500 kDa scaffold. A and B (and their respective controls E and F) have fixed molar ratios of dextran: antibody of 1:1; B and D (and their respective controls G and H) have fixed molar ratios of dextran: antibody of 3:1.
Figure 7:
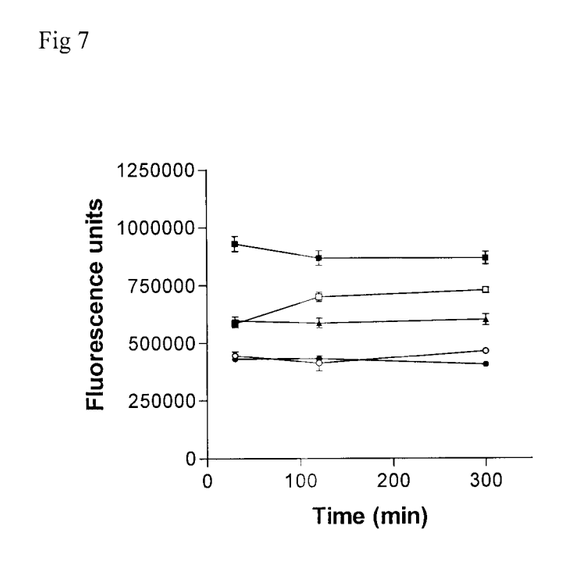
FIG. 7 is a graph showing a time course of fluorescence output from a fixed amount of poly-maleimido fluoresceinylated 400-500 kDa dextran scaffold after dissolution of freeze-dried material in either water (control; closed circles) or 200 mM Hepes/1 mM EDTA, pH 7.0, followed by treatment with various agents: 1.43 mM mercaptoethanol/5 mM glycine (closed squares), 0.143 mM mercaptoethanol/5 mM glycine (open squares), glycine 5 mM (triangles), or water (open circles).

Conjugates were tested on rabbit IgG-coated plates (Example 2) as described in Example 3. As can be seen in FIG. 6, with an antibody:dextran molar ratio of 1:1, the signal obtained with the 400-500kDa dextran conjugate (bar B) is over twice the signal for the 150 kDa dextran conjugate (bar A), reflecting the larger surface area and greater number of attached dye molecules per molecule of dextran. The differences are less pronounced when the dextran scaffolds are in 3:1 molar excess, but the fluorescence signal for the 400-500 kDa dextran (bar D) is still significantly higher than that for the 150 kDa dextran (bar C). Multiple attachment of the smaller scaffold (bar C; 3:1 dextran:Ab ratio) gives a conjugate that has a signal almost as great that prepared with the 400-500 kDa scaffold at a 1:1 dextran:Ab molar ratio. Fluorescence signals on control wells were low for all four conjugates (bars E, F, G and H).

Example 14

Quenching Effects of SMCC

Samples of polymalemido-fluoresceinylated dextran scaffolds (Example 13) were taken up in 40 µl of either 200 mM Hepes/1 mM EDTA, pH 7.0 or water (control, pH 5.8). Samples taken up in Hepes buffer were treated with 4 µl of various agents: 14.3 mM mercaptoethanol/50 mM glycine, pH 2.3; 1.43 mM mercaptoethanol/50 mM glycine pH 2.3; 50 mM glycine pH 7.5, or water. Samples were diluted to give signals within the linear range of the fluorescence plate reader. The results are shown in FIG. 6. Fluorescence was significantly increased by mercaptoethanol, the process being complete within 30 min (1.43 mM final concentration). Higher concentrations did not increase fluorescence further (not shown). A final concentration of 0.143 mM was insufficient to give maximal fluorescence, and it took at least 120 minutes for stable signal to be achieved. Addition of glycine, which accelerates the decay of 2-iminothiolane releasing low molecular weight thiols, also enhanced fluorescence. This enhancement was complete within 30 min but significantly less pronounced than with high concentrations of mercaptoethanol. There was no change in fluorescence over time at pH 5.8; at neutral pH values, in the absence of glycine or mercaptoethanol a slight increase in fluorescence was noted after 5 hours, which is perhaps explained by a slow decay of the maleimide functions. It is not clear why SMCC quenches the fluorescence of polymalemido-fluoresceinylated scaffolds but the effect is readily reversed using a mixture of mercaptoethanol/glycine, which deactivates 2-iminothiolane and, through an addition reaction with thiols, rapidly relieves the quenching effect of excess maleimido functions.

The invention claimed is:

1. A kit for use in a method of indirectly coupling a ligand to a polypeptide to be labelled with the ligand; the kit comprising
 a freeze-dried aliquot comprising both (a) an isolated scaffold molecule which is covalently attached to at least one said ligand and a plurality of thiol-reactive groups reactive towards a thiol group to be formed in situ on the polypeptide to be labelled; and (b) a thiol-generator comprising 2-iminothiolane, for in situ creation of thiol groups on the polypeptide to be labelled
 wherein said ligand comprises a molecule selected from the group consisting of biotin, avidin, fluorescent dye, chromophore, biotin attached with N-hydroxysuccinimide, biotin attached with maleimide, avidin attached with N-hydroxysuccinimide, and avidin attached with maleimide.

2. The kit according to claim 1, wherein at least one of the reagent components of the kit is present in a plurality of aliquots.

3. The kit according to claim 1, wherein the isolated scaffold molecule comprises dextran or a dextran derivative.

4. The kit according to claim 1, further comprising (d) at least one aliquot of glycine and a thiol to terminate the indirect coupling reaction.

5. The kit according to claim 4, wherein the glycine and thiol are present as a mixture comprising 25 to 100 mM glycine pH 2.0-2.6 and 5 to 25 mM thiol.

6. The kit according to claim 1, wherein the isolated scaffold molecule is larger than the ligand.

7. The kit according to claim 1, wherein said ligand comprises the molecule selected from the group consisting of biotin, avidin, chromophore, biotin attached with N-hydroxysuccinimide, biotin attached with maleimide, avidin attached with N-hydroxysuccinimide, and avidin attached with maleimide.

8. The kit according to claim 1, wherein the isolated scaffold molecule is ovalbumin.

9. The kit according to claim 1, wherein the fluorescent dye is selected from the group consisting of 5-(and-6)-Carboxyfluorescein; 5-(and-6)-Carboxyrhodamine 110; 5-(and-6)-Carboxyrhodamine 6G; 5-(and-6)-Carboxytetramethylrhodamine; 5-(and-6)-Carboxy-X-rhodamine; 5-Carboxyfluorescein (5-FAM); 5-Carboxyrhodamine 110; 5-Carboxyrhodamine 6G; 5-Carboxytetramethylrhodamine; 5-Carboxy-X-rhodamine; 6-((7-Amino-4-methylcoumarin-3-acetyl)amino)hexanoic acid; 6-(Fluorescein-5-carboxamido)hexanoic acid; 6-carboxy-2",4,4",5",7,7"-hexachlorofluorescein; 6-Carboxy-4",5"-dichloro-2",7"-dimethoxyfluorescein (JOE); 6-Carboxyfluorescein (6-FAM); 6-Carboxyrhodamine 110; 6-Carboxyrhodamine 6G; 6-Carboxytetramethylrhodamine; 6-Carboxy-X-rhodamine; 7-Hydroxycoumarin-3-carboxylic acid; 7-Methoxycoumarin; Alexa Fluor 350; Alexa Fluor 405; Alexa Fluor 430; Alexa Fluor 488; Alexa Fluor 514; Alexa Fluor 532; Alexa Fluor 546; Alexa Fluor 555; Alexa Fluor 568; Alexa Fluor 594; Alexa Fluor 633; Alexa Fluor 647; Alexa Fluor 660; Alexa Fluor 680; Alexa Fluor 700; Alexa Fluor 750; Alexa Fluor 790; AMCA (7-amino-4-methylcoumarin-3-acetic acid); ATTO 390; ATTO 425; ATTO 465; ATTO 488; ATTO 495; ATTO 520; ATTO 532; ATTO 550; ATTO 565; ATTO 590; ATTO 594; ATTO 610; ATTO 611X; ATTO 620; ATTO 633; ATTO 635; ATTO 637; ATTO 647; ATTO 647N; ATTO 655; ATTO 680; ATTO 700; ATTO 725; ATTO 740; Bodipy dyes; Cascade Blue; Cascade Yellow; Chromeo 488; Chromeo 494; Chromeo 546; Chromeo 642; Cy2 bis; Cy3 mono; Cy3.5 mono; Cy5 mono; Cy5.5 mono; Cy7 mono; DyLight 488; DyLight 549; DyLight 549; DyLight 649; DyLight 680; DyLight 800; Fluorescein; HiLyte Fluor 488HiLyte Fluor 555; HiLyte Fluor 647; HiLyte Fluor 680; HiLyte Fluor 750; IRDye 700DX; IRDye 800CW; IRDye 800RS; Lucifer yellow; Marina Blue; Oregon Green 488; Pacific Blue; Pacific Orange; PF-415; PF-488; PF-488-LSS; PF-500-LSS; PF-505; PF-510-LSS; PF-514-LSS; PF-520-LSS; PF-546; PF-555; PF-590; PF-610; PF-633; PF-647; PF-680; PF-700; PF-750; PF-780; PURETIME 14; PURETIME 20; PURETIME 22; PURETIME 325; Pyrene; Rhodamine B; Sulforhodamine 101; Sulforhodamine B ; and Tetramethylrhodamine.

10. The kit according to claim 1, further comprising another freeze-dried aliquot.

11. The kit according to claim 1, wherein the kit comprises more than one of said freeze-dried aliquot.

* * * * *